US011564887B2

(12) United States Patent
Achkar et al.

(10) Patent No.: US 11,564,887 B2
(45) Date of Patent: Jan. 31, 2023

(54) PROCESS FOR THE PRODUCTION OF COMPRESSED TABLETS

(71) Applicant: DSM IP ASSETS B.V., Heerlen (NL)

(72) Inventors: Jihane Achkar, Kaiseraugst (CH); Sylvain Diguet, Kaiseraugst (CH); Bruno Leuenberger, Kaiseraugst (CH); Loni Schweikert, Kaiseraugst (CH); Olivia Vidoni, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 92 days.

(21) Appl. No.: 17/237,976

(22) Filed: Apr. 22, 2021

(65) Prior Publication Data

US 2021/0236431 A1  Aug. 5, 2021

Related U.S. Application Data

(62) Division of application No. 15/763,525, filed as application No. PCT/EP2016/072685 on Sep. 23, 2016, now Pat. No. 11,033,500.

(30) Foreign Application Priority Data

Oct. 2, 2015 (EP) ..................... 15188063

(51) Int. Cl.
| | |
|---|---|
| *A61K 9/20* | (2006.01) |
| *A61K 9/50* | (2006.01) |
| *A61K 31/015* | (2006.01) |
| *A61K 31/047* | (2006.01) |
| *A61K 31/07* | (2006.01) |
| *A61K 31/122* | (2006.01) |
| *A61K 31/197* | (2006.01) |
| *A61K 31/355* | (2006.01) |
| *A61K 31/375* | (2006.01) |
| *A61K 31/4188* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 31/593* | (2006.01) |
| *A61K 31/675* | (2006.01) |
| *A61K 31/714* | (2006.01) |
| *A61K 33/00* | (2006.01) |
| *A61K 33/04* | (2006.01) |
| *A61K 33/06* | (2006.01) |
| *A61K 33/18* | (2006.01) |
| *A61K 33/26* | (2006.01) |
| *A61K 33/30* | (2006.01) |
| *A61K 33/34* | (2006.01) |

(52) U.S. Cl.
CPC .......... *A61K 9/2095* (2013.01); *A61K 9/2009* (2013.01); *A61K 9/2013* (2013.01); *A61K 9/2054* (2013.01); *A61K 9/2081* (2013.01); *A61K 9/5063* (2013.01); *A61K 9/5089* (2013.01); *A61K 31/015* (2013.01); *A61K 31/047* (2013.01); *A61K 31/07* (2013.01); *A61K 31/122* (2013.01); *A61K 31/197* (2013.01); *A61K 31/355* (2013.01); *A61K 31/375* (2013.01); *A61K 31/4188* (2013.01); *A61K 31/455* (2013.01); *A61K 31/51* (2013.01); *A61K 31/519* (2013.01); *A61K 31/525* (2013.01); *A61K 31/593* (2013.01); *A61K 31/675* (2013.01); *A61K 31/714* (2013.01); *A61K 33/00* (2013.01); *A61K 33/04* (2013.01); *A61K 33/06* (2013.01); *A61K 33/18* (2013.01); *A61K 33/26* (2013.01); *A61K 33/30* (2013.01); *A61K 33/34* (2013.01)

(58) Field of Classification Search
CPC combination set(s) only.
See application file for complete search history.

(56) References Cited

U.S. PATENT DOCUMENTS

| 2012/0093974 A1 | 4/2012 | Wright et al. |
| 2012/0237602 A1 | 9/2012 | Ikeda |
| 2014/0242179 A1 | 8/2014 | Diguet |

FOREIGN PATENT DOCUMENTS

| EP | 2 554 185 | 2/2013 |
| JP | 2004-175713 | 6/2004 |
| JP | 2012-34614 | 2/2012 |
| JP | 2014-534959 | 12/2014 |
| JP | 2015-86171 | 5/2015 |
| WO | 2013/053793 | 4/2013 |

OTHER PUBLICATIONS

Notice of Reasons for Rejection for JP Patent Appln No. P2018-516061 dated Mar. 16, 2020 (with English-language translation).
Clinical Pharmacology and Therapy, vol. 19, No. 6, p. 405-419, 2009.
Watanabe et al., "Manufacturing Process for Compressed Tablets," 2009.
Watanabe et al.; "Manufacturing Process for Compressed Tablets," Clinical Pharmacology and Therapy, vol. 19, No. 6, p. 405-419, 2009. (English translation).
International Search Report for PCT/EP2016/072685, dated Nov. 25, 2016, 3 pages.
Written Opinion of the ISA for PCT/EP2016/072685, dated Nov. 25, 2016, 5 pages.
Notice of Reasons for Rejection for JP Patent Appln No. P2018-516061 dated Aug. 18, 2020 (with English-language translation).

*Primary Examiner* — Hasan S Ahmed
(74) *Attorney, Agent, or Firm* — Nixon & Vanderhye P.C.

(57) ABSTRACT

The present patent application relates a process for the production of compressed tablets using specific coated particles, wherein the coating (system) comprises at least one wax and/or at least one fat. Furthermore it relates to compressed (compacted) tablets and as well as to specific coated particles.

10 Claims, 1 Drawing Sheet

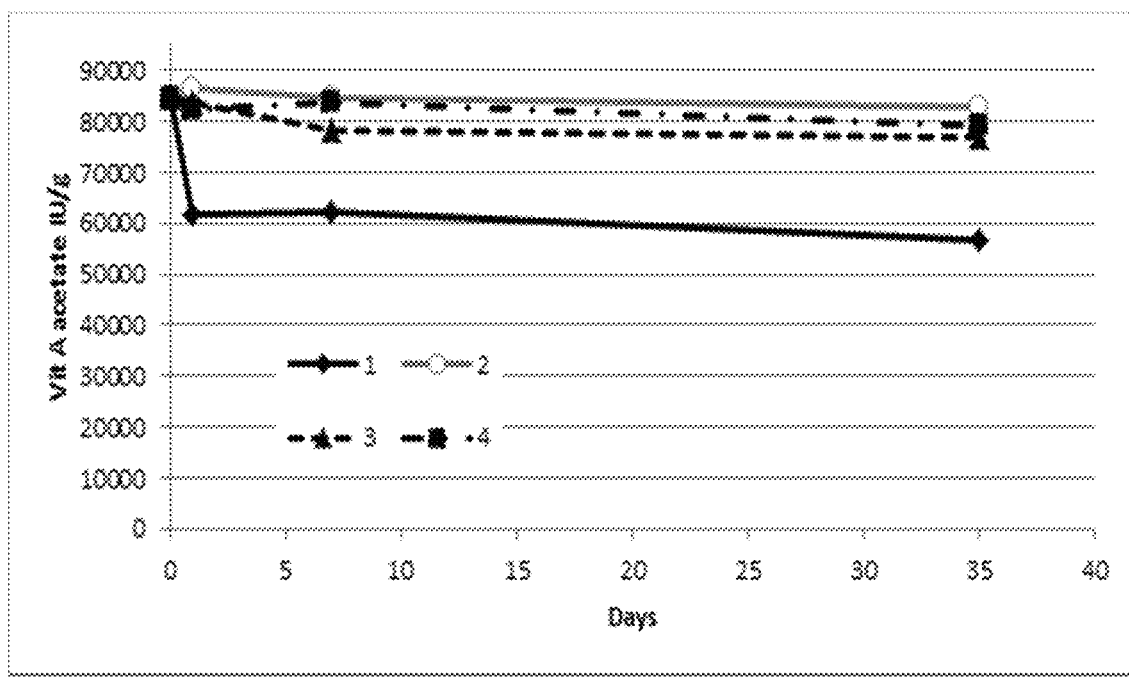
1: uncoated particles; 2: particles coated with palm oil FH; 3: particles coated with carnauba wax; 4: particles coated with sugarcane wax

PROCESS FOR THE PRODUCTION OF COMPRESSED TABLETS

This application is a divisional of commonly owned U.S. Ser. No. 15/763,525 filed Mar. 27, 2018 (now U.S. Pat. No. 11,033,500), which is the U.S. national phase of International Application No. PCT/EP2016/072685 filed Sep. 23, 2016, which designated the U.S. and claims priority to EP Patent Application No. 15188063.0 filed Oct. 2, 2015, the entire contents of each of which are hereby incorporated by reference.

The present patent application relates a process for the production of compressed tablets using specific coated particles, wherein the coating (system) comprises at least one wax and/or at least one fat. Furthermore it relates to compressed (compacted) tablets and as well as to specific coated particles.

Particles which are used to be compacted into tablets usually contain one or more active ingredient, which are essential for the tablet (for need of the consumers). Examples for such active ingredients are vitamins, carotenoids, oils, minerals, plants extracts or any other commonly used active ingredient. These active ingredients are first formulated into particles, which are then used for (for example) producing compressed (compacted) tablets or they are used in premixes which are then used for further formulations (such as compressed or compacted tablets).

A major problem and disadvantage in the use of such particles is that when pressure (usually more than 5 kN) is applied on such particles (which comprise the essential ingredients for the tablet), then some of the essential ingredients are usually squeezed out of the particle, degraded within days and lost for further formulation. Furthermore, a smell issue or a discoloration issue can also arise because of this "squeezing-out"-phenomenon, depending on the active ingredient. This well-known effect is called "initial loss".

To assure that in the final product (for example a compressed or compacted tablet) the correct e.g. desired) amount of the essential ingredient is present, an overdosage of the essential ingredient is usually used nowadays. But overdosage is not an ideal solution of this problem.

There are disadvantages, which are connected to overdosage, such as
  (i) waste of material (essential ingredients), which can be expensive;
  (ii) the essential ingredients can have a bad smell, so that the particles need to be washed before they are compacted, this an additional process step;
  (iii) the "squeezed-out" ingredients can cause an issue when used for further formulations;
  (iv) difficult to determine the (more or less) exact content of the essential ingredient in the compressed tablet;
  (v) regulatory constraints regarding upper limits of some essential ingredients inclusion in formulations or final products such as compacted tablets.

Therefore the goal of the present invention was to find a way to provide particles, which show less initial loss when compressed (compacted) into tablets. The terms "compressed" and "compacted" (as well as their verbs "compress" and "compact") do mean the same in the context of the present invention.

It was found when the particles comprising at least one active ingredient are coated with at least one wax and/or at least one fat, then the initial loss is lowered significantly.

Coating of particles is a well-known principle. It is used in many fields of applications.

Coating systems (or coatings) are usually used to protect particles against any kind of external influence. It is usually the goal of a coating to keep the particles as intact as possible.

Now it was the goal to find a coating system, which is not too brittle to be compacted and furthermore wherein afterwards the coated particles are in a free-flowing powder form, which is easy to handle.

Now it was found when at least one specific wax and/or at least one fat is used to coat particles which comprise at least one active ingredient, then it is possible to compact or press these coated particles into tablets, whereby the initial loss is reduced significantly, and also the overall properties of the powder form are excellent.

Therefore the present invention relates to a process (P) for the production of compressed tablets, wherein coated particles comprising
  (i) 40 wt-%-95 wt-%, based on the total weight of the coated particle, of a core, comprising at least one active ingredient and
  (ii) 5 wt-%-60 wt-%, based on the total weight of the coated particle, of a coating system, and said coating system comprises at least one wax and/or at least one fat,
  are compressed with a pressure of a least 5 kN.

All percentages in the present patent application always add up to 100.

Furthermore the present invention relates to a process (P') for the production of compressed tablets, wherein coated particles consisting of
  (iii) 40 wt-%-95 wt-%, based on the total weight of the coated particle, of a core, comprising at least one active ingredient and
  (iv) 5 wt-%-60 wt-%, based on the total weight of the coated particle, of a coating system, and said coating system comprises at least one wax and/or at least one fat,
  are compressed with a pressure of at least 5 kN.

To produce compress tablets a pressure of 5-40 kN is usually applied.

Therefore the present invention relates to a process (P1), which is process (P) or (P'), wherein a pressure of 5-40 kN is usually applied.

The size of the compress tablets can vary and depends on the use of the tablets. Usually they are several millimeter in size. Also the shape of the compressed tablet can vary (sphere like, egg-like, etc).

The size and the shape of the compressed tablets are not essential features of the present invention.

The compressed tablets could also have an additional coating. This is an non-essential feature.

The term "coated particle" in the context always refers to a core which is coated by a coating system.

The term "core" in the context of the present invention always refers to a particle, which is produced by any commonly known and used technology (such as spray drying, spray cooling, spray chilling etc.) and which contains at least one active ingredient.

The term "compressed tablets" or "compacted tablets" (both terms mean the same) in the context of the present invention refers to tablets which are produced by applying pressure in their production.

The size of the core as well as the size of the coated particle is not an essential feature of the present invention.

The coated particles are usually of such a size that tablets can be compacted.

A suitable size is between 50-1000 μm (preferably 100-800 μm); the size is defined by the diameter of the longest dimension of the particle and measured by commonly known method (like light scattering).

The distribution of the particle size is also no essential feature of the present invention.

The shape of the core as well as of the coated particles which are used in the process according to the present invention, is also not an essential feature of the present invention. The shape can be sphere-like or any other form (also mixtures of shapes). Usually and preferably the particles are sphere-like.

The coating system of the coated particle, which are used in the process according to the present invention, is layered around the core. Usually (and ideally) the coating covers the whole surface of the particle. Furthermore, the layer is usually (and ideally) equally thick on the surface of the core.

Waxes in the context of the present invention are organic compounds that characteristically consist of long alkyl chains. Natural waxes (plant, animal) are typically esters of fatty acids and long chain alcohols. Synthetic waxes are long-chain hydrocarbons lacking functional groups.

Fats, which are used for the embodiments of the present invention, consist of a wide group of compounds that are generally soluble in organic solvents and largely insoluble in water. Hydrogenated fats (or saturated fats) in the context of the present invention are generally triesters of glycerol and fatty acids. Fatty acids are chains of carbon and hydrogen atoms, with a carboxylic acid group at one end. Such fats can have natural or synthetic origin. It is possible to hydrogenate a (poly)unsaturated fat to obtain a hydrogenated (saturated) fat.

Especially suitable waxes and fats have a dropping point of from 30 to 85° C., preferably 40 to 70° C.

The dropping point of a material is that temperature (in ° C.) when the material begins to melt under standardized conditions. The material is heated so long until it changes the state of matter from solid to liquid. The dropping point is the temperature when the first dropping is released from the material. The determination of the dropping point (Tropfpunkt) is carried out as described in the standard norm DIN ISO 2176.

Preferred examples of waxes and fats suitable for the present invention are glycerine monostearate, carnauba wax, candelilla wax, sugarcane wax, palmitic acid, stearic acid, (fully) hydrogenated cottonseed oil, (fully) hydrogenated palm oil and (fully) hydrogenated rapeseed oil. These compounds can be used as such or as mixtures. Preferred are carnauba wax, candelilla wax, sugarcane wax and (fully) hydrogenated palm oil.

Therefore the present invention relates to a process (P2), which is process (P), (P') or (P1), wherein the coating system of the coated particles comprises at least one wax and/or at least one fat, which has a dropping point of from 30 to 85° C., preferably 40 to 70° C.

Therefore the present invention relates to a process (P3), which is process (P), (P'), (P1) or (P2), wherein the coating system of the coated particles comprises at least one wax and/or at least one fat chosen from the group consisting of glycerine monostearate, carnauba wax, candelilla wax, sugarcane wax, palmitic acid, stearic acid, (fully) hydrogenated cottonseed oil, (fully) hydrogenated palm oil and (fully) hydrogenated rapeseed oil.

Therefore the present invention relates to a process (P3'), which is process (P), (P'), (P1) or (P2), wherein the coating system of the coated particles comprises at least one wax and/or at least one fat chosen from the group consisting of carnauba wax, candelilla wax, sugarcane wax and (fully) hydrogenated palm oil.

In a preferred embodiment of the present invention the coated particles, which are used in the process according to the present invention, comprises 50 wt-%-90 wt-%, based on the total weight of the coated particle, of a core and 10 wt-%-50 wt-15%, based on the total weight of the coated particle, of a coating system; more preferred 60 wt-%-80 wt-%, based on the total weight of the coated particle, of a core and 20 wt-%-40 wt-%, based on the total weight of the coated particle, of a coating system.

Therefore the present invention relates to a process (P4), which is process (P), (P'), (P1), (P2) or (P3), wherein the coating system of the coated particles comprises 50 wt-%-90 wt-%, based on the total weight of the coated particles, of a core and 10 wt-%-50 wt-%, based on the total weight of the coated particles, of a coating system.

Therefore the present invention relates to a coated particle (P4'), which is process (P), (P'), (P1), (P2), (P3) or (P3'), wherein the coated particles comprise 60 wt-%-80 wt-%, based on the total weight of the coated particles, of a core and 20 wt-%-40 wt-%, based on the total weight of the coated particles, of a coating system.

The coating system of the coated particles can also comprise further ingredients, which are non-essential for the present invention. Such ingredients can be dyes, flavours, or any other ingredient, which can have a purpose in the compressed tablet.

The core of the coated particles comprises at least one active ingredient, which is needed in the compressed tablet.

The amount in the compressed tablet of the active ingredient(s) can vary and it depends on factors such as for example on the type of active ingredient, on the use of the tablet etc.

The amount of the active ingredient(s) in compressed tablets according to the present invention can be influenced and controlled by the amount of the at least one active ingredient in the core and by the amount of core in relation to coating and finally the amount of the coated particle in the process of production of the compressed tablet.

That active ingredient (or mixture of active ingredients) can be any kind of active ingredient. The ingredients can be oil-soluble or water-soluble.

Suitable ingredients are for example any vitamins, carotenoids, minerals, plant extracts or any other active ingredient.

Suitable ingredients are fat-soluble vitamins, such a vitamin A, D, E, and K (as well as derivatives thereof); water-soluble vitamins such as B-vitamins and vitamin C; and carotenoids such as $\alpha$-carotene, $\beta$-carotene, 8'-apo-$\beta$-carotenal, 8'-apo-$\beta$-carotenoic acid esters, canthaxanthin, astaxanthin, lycopene, lutein, zeaxanthin and crocetin.

Preferred active ingredients in the context of the present invention are fat-soluble vitamins. These are vitamins A, D, E, and K (as well as derivatives of any of these vitamins). Especially preferred is vitamin A and/or its derivatives.

Therefore the present invention relates to a process (P5), which is process (P), (P'), (P1), (P2), (P3), (P3'), (P4) or (P4'), wherein the core of the coated particles comprises at least one active ingredient chosen form the group consisting of vitamins, carotenoids, minerals and plant extracts.

Therefore the present invention relates to a process (P5'), which is process (P5), wherein the core of the coated particles comprises at least one active ingredient chosen form the group consisting of fat-soluble vitamins, such a vitamin A, D, E, and K (as well as derivatives thereof);

water-soluble vitamins such as B vitamins and vitamin C; and carotenoids such as α-carotene, β-carotene, 8'-apo-β-carotenal, 8'-apo-β-carotenoic acid esters, canthaxanthin, astaxanthin, lycopene, lutein, zeaxanthin and crocetin.

Therefore the present invention relates to a process (P5"), which is process (P5), wherein the core comprises at least one active ingredient chosen form the group consisting of vitamins A, D, E, and K (as well as derivatives of any of these vitamins).

Therefore the present invention relates to a process (P5'''), which is process (P5), wherein the core comprises vitamin A and/or its derivatives.

The amount of the active ingredient in the core of the coated particles, which are used in the process according to the present invention can vary. The amount can be up to 75 wt-%, based on the total weight of the core, of at least one active ingredient. Usually the core comprise at least 0.5 wt-%, based on the total weight of the core, of at least one active ingredient. The content is dependent on the kind of active ingredient (or the mixture of active ingredients) which is used. It could also be higher as well lower.

A very usual range of an amount of the active ingredient in the core is from 0.5-40 wt-%, based on the total weight of the core.

Another very usual range of an amount of the active ingredient in the core is from 0.5-20 wt-%, based on the total weight of the core.

Therefore the present invention relates to a process (P6), which is process (P), (P'), (P1), (P2), (P3), (P3'), (P4), (P4'), (P5), (P5'), (P5") or (P5'''), wherein the amount of the at least one active ingredient in the core of the coated particles is up to 75 wt-%, based on the total weight of the core.

Therefore the present invention relates to a process (P6'), which is process (P), (P'), (P1), (P2), (P3), (P3'), (P4), (P4'), (P5), (P5'), (P5"), (P5''') or (P6), wherein the amount of the at least one active ingredient in the core is at least 0.5 wt-%, based on the total weight of the core.

Therefore the present invention relates to a process (P6"), which is process (P), (P'), (P1), (P2), (P3), (P3'), (P4), (P4'), (P5), (P5'), (P5) or (P5'''), wherein the amount of the at least one active ingredient in the core of the coated particles is 0.5 wt-%-40 wt-%, based on the total weight of the core.

Therefore the present invention relates to a process (P6'''), which is process (P), (P'), (P1), (P2), (P3), (P3'), (P4), (P4'), (P5), (P5'), (P5) or (P5'''), wherein the amount of the at least one active ingredient in the core of the coated particles is 0.5 wt-%-20 wt-%, based on the total weight of the core.

The core of the coated particles used in the process according to the present invention can comprise other components which are used to produce particles (by spray drying, spray cooling, spray chilling, etc), which comprise the active ingredient (s).

The term "core" in the context of the present invention always refers to a particle, which is produced by any commonly known and used technologies (such as spray drying, spray cooling, spray chilling etc.) and which contains at least one active ingredient as defined above.

The coated particles, which are used according to the present invention can be produced by any commonly known process, which are used to produce such particles (such as spray chilling, spray coating, fluidized bed spray granulation, film coating, etc).

It is possible to produce the particles first and then coat them at a later stage or to do both steps in one process (production of the particles and then coat them right away).

It also possible to add any additional ingredients, excipients and/or auxiliary agents to produce the compressed tablets. These are the usual compounds which are used to compress tablets. Such compounds (excipients) are for example, fillers (such as microcrystalline cellulose), acidity regulators (such as calcium phosphate), anti-adherent (such as magnesium stearate), dyes, flavours, sweeteners, etc. The amount of these compounds in the process according to the present invention can vary and depends on the compressed tablets which is produced and the coated particles which are used.

It is also possible to add any kind active ingredients to the tablets as well.

A usual amount of these ingredients is up to 99.9 wt-%, based on the total weight of the compressed tablets.

Therefore the present invention relates to a process (P7), which is process (P), (P'), (P1), (P2), (P3), (P3'), (P4), (P4'), (P5), (P5'), (P5"), (P5'''), (P6), (P6'), (P6") or (P6'''), wherein 0.1-40 wt-%, based on the total weight of the compressed tablets, of the coated particles and 60-99.9 wt-%, based on the total weight of the compressed tablets, of at least additional ingredient, excipient and/or auxiliary agent is used.

The percentages add up to 100%.

Therefore the present invention relates to a process (P7'), which is process (P7), wherein 0.5-30 wt-%, based on the total weight of the compressed tablets, of the coated particles and 70-99.5 wt-%, based on the total weight of the compressed tablets, of at least additional ingredient, excipient and/or auxiliary agent chosen from the group consisting of fillers (such as microcrystalline cellulose), acidity regulators (such as calcium phosphate), anti-adherent (such as magnesium stearate), dyes, flavours and sweeteners are used.

As stated above the main advantage of the embodiments of the present invention is that the initial loss of the coated particles according to the present invention when compacted (into a tablet) is significantly lower as of the particles of the prior art.

The pressure which is used is to produce tablets is usually between 5 and 40 kN. The tablets can be produce by commonly known and used tablet pressing devices.

Furthermore, the present invention relates to the compress tablets obtained by the process according to the present invention.

The present invention also relates to compressed tablets (CT) comprising (i) 0.1-40 wt-%, based on the total weight of the compressed tablets, of the coated particles, which comprise 40 wt-%-95 wt-%, based on the total weight of the coated particle, of a core, comprising at least one active ingredient and 5 wt-%-60 wt-%, based on the total weight of the coated particle, of a coating system, and said coating system comprises at least one wax and/or at least one fat, and (ii) 60-99.9 wt-%, based on the total weight of the compressed tablets, of at least one additional ingredient, excipient and/or auxiliary agent chosen from the group consisting of fillers (such as microcrystalline cellulose), acidity regulators (such as calcium phosphate), anti-adherent (such as magnesium stearate), dyes, flavours and sweeteners.

All preferences defined above for the coated particles used in the process according to the present invention also relates to the compressed tablets defined herein.

The present invention also relates to compressed tablets (CT1) comprising
  (i) 0.1-40 wt-%, based on the total weight of the compressed tablets, of the coated particles, which comprise 40 wt-%-95 wt-%, based on the total weight of the coated particle, of a core, comprising vitamin A and/or its derivative and 5 wt-%-60 wt-%, based on the total weight of the coated particle, of a coating system consisting of carnauba wax, candelilla wax, sugarcane wax and/or (fully) hydrogenated palm oil, and
  (ii) 60-99.9 wt-%, based on the total weight of the compressed tablets, of at least one additional ingredient, excipient and/or auxiliary agent chosen from the group consisting of fillers (such as microcrystalline cellulose), acidity regulators (such as calcium phosphate), anti-adherent (such as magnesium stearate), dyes, flavours and sweeteners.

The percentages add up to 100%.

Furthermore the present invention relates to coated particles (CP) comprising
  (i) 40 wt-%-95 wt-%, based on the total weight of the coated particle, of a core, comprising at least one active ingredient chosen from the group consisting of vitamin A, D, E, and K (preferably is vitamin A and/or its derivative), and
  (ii) 5 wt-%-60 wt-%, based on the total weight of the coated particle, of a coating system which is chosen form the groups consisting of glycerine monostearate, carnauba wax, candelilla wax, sugarcane wax, palmitic acid, stearic acid, (fully) hydrogenated cottonseed oil, (fully) hydrogenated palm oil and (fully) hydrogenated rapeseed oil.

All percentages in the present patent application always add up to 100.

Furthermore the present invention relates to coated particles (CP') consisting of
  (i) 40 wt-%-95 wt-%, based on the total weight of the coated particle, of a core, comprising at least one active ingredient chosen from the group consisting of vitamin A, D, E, and K (preferably is vitamin A and/or its derivative), and
  (ii) 5 wt-%-60 wt-%, based on the total weight of the coated particle, of a coating system which is chosen form the groups consisting of glycerine monostearate, carnauba wax, candelilla wax, sugarcane wax, palmitic acid, stearic acid, (fully) hydrogenated cottonseed oil, (fully) hydrogenated palm oil and (fully) hydrogenated rapeseed oil.

Furthermore the present invention relates to coated particles (CP1) comprising
  (iii) 40 wt-%-95 wt-%, based on the total weight of the coated particle, of a core, comprising vitamin A and/or its derivative, and
  (iv) 5 wt-%-60 wt-%, based on the total weight of the coated particle, of a coating system which is chosen form the groups consisting of carnauba wax, candelilla wax, sugarcane wax and (fully) hydrogenated palm oil.

All percentages in the present patent application always add up to 100.

Furthermore the present invention relates to coated particles (CP1') consisting of
  (i) 40 wt-%-95 wt-%, based on the total weight of the coated particle, of a core, comprising vitamin A and/or its derivative, and
  (ii) 5 wt-%-60 wt-%, based on the total weight of the coated particle, of a coating system which is chosen form the groups consisting of carnauba wax, candelilla wax, sugarcane wax and (fully) hydrogenated palm oil.

FIGURES

FIG. 1: storage stability of the coated particles according to the present invention as well as the storage stability of an uncoated particle.

The invention is illustrated by the following Example. All temperatures are given in ° C. and all parts and percentages are related to the weight.

EXAMPLES

Example 1

A total of 300 g of particle containing vitamin A acetate having a particle size distribution between 150 μm and 600 μm were coated on a fluidized bed coating using bottom spray set up. The cores were introduced into the reactor at room temperature and conditioned at the desired temperature before spraying the wax material. Carnauba wax (128.6 g) was molten beforehand at 95° C. and sprayed at a rate of about 3 g·min$^{-1}$. The entire process was concluded after approximately 50 min. Then the product was cooled down to RT in the reactor and the collected product was sieved to isolate the fraction between 160 to 500 μm in size. The use of sugarcane wax led to an end product containing large quantity of agglomerates. In the case of microcrystalline wax, the product became too sticky to be processed to the end. The same procedure was followed for the fully hydrogenated palm oil (palm oil FH); in this case the material was also molten at 95° C.

|  | Carnauba wax % | Sugarcane wax % | Palm oil FH % |
|---|---|---|---|
| <160 μm | 0.1 | 0.3 | 0.1 |
| 160-500 μm | 84.4 | 54.9 | 98.7 |
| >500 μm | 15.5 | 44.8 | 1.2 |
| Total | 100 | 100 | 100 |

Example 2

100 g of powder consisting of 13.52 g of the coated vitamin A acetate particles (potency: 500'000 IU/g), 33.24 g microcrystalline cellulose, 49.86 g calcium phosphate and 0.2 g of magnesium stearate was mixed during 10 min. The amount of product form to be added to the mixture was calculated to get a tablet with 84'500 IU/g of vitamin A acetate. This end preparation was then compressed with a pressure of 35 KN. The tablets (common disk-shaped; 0.2 g) were stored at room temperature in a closed brown-glass bottle and the vitamin A acetate content determined after 1, 7 and 35 days of storage.

The initial loss of the coated particles according to the present invention is far lower than those of the prior art particles. This can be seen in FIG. 1, where all values are listed.

Example 3

The following table represents a typical multivitamin/multimineral tablet composition.

The tablets are made by tableting machine (Korsch XL 100) in a 22×9 mm oblong form. The compression force was 17.5 kN.

TABLE

Typical multivitamin/Multimineral tablet composition

| | Ingredient | content mg or IU |
|---|---|---|
| 1 | Vitamin A (in the coated form of Example 1) | 3000 IU |
| 2 | Beta Carotene | 2000 IU |
| 3 | Zeaxanthin | 1.0 |
| 4 | Vitamin $D_3$ | 400 IU |
| 5 | Vitamin C | 60.0 |
| 6 | Vitamin E | 30 IU |
| 7 | Vitamin $B_1$ (Thiamine) | 1.5 |
| 8 | Vitamin $B_2$ | 1.7 |
| 9 | Vitamin $B_3$ (Niacinamide) | 20.0 |
| 10 | Vitamin $B_5$ (Pantothenic Acid) | 10.0 |
| 11 | Vitamin $B_6$ (Pyridoxol) | 2.0 |
| 12 | Vitamin $B_8$ (Biotin) | 0.03 |
| 13 | Vitamin $B_9$ (Folic Acid) | 0.4 |
| 14 | Vitamin $B_{12}$ | 0.006 |
| 15 | Vitamin $K_1$ | 0.025 |
| 16 | Iron | 18.0 |
| 17 | Copper | 2.0 |
| 18 | Manganese | 2.0 |
| 19 | Zinc | 15.0 |
| 20 | Iodine | 0.15 |
| 21 | Chrome | 0.06 |
| 22 | Selenium | 0.05 |
| 23 | Molybdene | 0.075 |
| 24 | Potassium Chloride | 40.0 |
| 25 | Magnesium | 100.0 |
| 26 | Calcium and Phosphorus | 162.0 |
| 27 | Crospovidone NF | 7.0 |
| 28 | Silicium | 2.00 |
| 29 | Stearic Acid[5] | 4.0 |
| 30 | Magnesium Stearate[6] | 4.0 |
| 31 | Cellulose, microcryst. | 346.85 |

The invention claimed is:

1. A compressed tablet comprising:
   (a) 0.1-40 wt. %, based on the total weight of the compressed tablet, of a powder composition comprising coated particles compressed at a pressure of 5 kN to 40 kN, wherein each of the coated particles comprises:
      (a1) 40 wt-%-95 wt-%, based on the total weight of the coated particle, of a core comprising at least one active ingredient selected from the group consisting of fat-soluble vitamins, water-soluble vitamins and carotenoids, and
      (a2) 5 wt-%-60 wt-%, based on the total weight of the coated particle, of a coating on the core which comprises a coating system comprised of at least one wax and/or at least one fat selected from the group consisting of glycerine monostearate, carnauba wax, candelilla wax, sugarcane wax, palmitic acid, stearic acid, (fully) hydrogenated cottonseed oil, (fully) hydrogenated palm oil, and (fully) hydrogenated rapeseed oil, and
   (b) 60-99.9 wt. %, based on the total weight of the compressed tablet, of at least one additional ingredient, excipient and/or auxiliary agent selected from the group consisting of fillers, acidity regulators, antiadherents, dyes, flavours and sweeteners, wherein the compressed tablet exhibits less initial loss after 35 days of the at least one active ingredient from the core as compared to an identical compressed tablet not comprising the coating on the core.

2. The compressed tablet according to claim 1, wherein the coated particles comprise, based on total weight of the coated particle, 50 wt. %-90 wt. % of the core and 10 wt. %-50 wt. % of the coating system.

3. The compressed tablet according to claim 1, wherein the at least one active ingredient in the core is selected from the group consisting of vitamins, carotenoids, minerals and plant extracts.

4. The compressed tablet according to claim 3, wherein the least one active ingredient is selected from the group consisting of fat-soluble vitamins, water-soluble vitamins; and carotenoids.

5. The compressed tablet according to claim 3, wherein the at least one active ingredient is selected chosen form the group consisting of vitamins A, D, E and K and derivatives thereof.

6. The compressed tablet according to claim 3, wherein the active ingredient core comprises vitamin A.

7. The compressed tablet according to claim 3, wherein the at least one active ingredient is a water-soluble vitamin selected from the group of consisting of B vitamins and vitamin C.

8. The compressed tablet according to claim 3, wherein the at least one active ingredient is a carotenoid selected from the group consisting of α-carotene, β-carotene, 8'-apo-β-carotenal, 8'-apo-β-carotenoic acid esters, canthaxanthin, astaxanthin, lycopene, lutein, zeaxanthin and crocetin.

9. A compressed tablet comprised of a plurality of coated particles compressed at a pressure of 5 kN to 40 kN, wherein each of the coated particles comprise:
   (i) 40 wt. %-95 wt. %, based on the total weight of the coated particle, of a core which comprises at least one active ingredient selected from the group consisting of vitamins A, D, E, and K, and
   (ii) 5 wt. %-60 wt. %, based on the total weight of the coated particle, of a coating system present as a coating on the core, wherein the coating system is includes at least one one wax and/or at least one fat selected from the group consisting of glycerine monostearate, carnauba wax, candelilla wax, sugarcane wax, palmitic acid, stearic acid, at least partially hydrogenated cottonseed oil, at least partially hydrogenated palm oil and at least partially hydrogenated rapeseed oil, wherein the compressed tablet exhibits less initial loss after 35 days of the at least one active ingredient from the core as compared to an identical compressed tablet not comprising the coating on the core.

10. A powder composition comprised of coated particles, wherein the coated particles consist of:
   (i) 40 wt. %-95 wt. %, based on the total weight of the coated particle, of a core which comprises at least one active ingredient selected from the group consisting of vitamins A, D, E, and K, and
   (ii) 5 wt. %-60 wt. %, based on the total weight of the coated particle, of a coating system present as a coating on the core, wherein the coating system is includes at least one one wax and/or at least one fat selected from the group consisting of glycerine monostearate, carnauba wax, candelilla wax, sugarcane wax, palmitic acid, stearic acid, at least partially hydrogenated cottonseed oil, at least partially hydrogenated palm oil and at least partially hydrogenated rapeseed oil, wherein a compressed tablet of the powder composition compressed at 5 kN to 40 kN exhibits less initial loss after 35 days of the at least one active ingredient from the core as compared to an identical compressed tablet not comprising the coating on the core.

\* \* \* \* \*